United States Patent [19]

Ose et al.

[11] Patent Number: 4,594,337
[45] Date of Patent: Jun. 10, 1986

[54] METHODS OF CONTROLLING MYCOPLASMA INFECTIONS

[75] Inventors: Earl E. Ose, Greenfield; Jan R. Turner, Carmel, both of Ind.

[73] Assignee: Eli Lilly and Company, Indianapolis, Ind.

[21] Appl. No.: 705,953

[22] Filed: Feb. 27, 1985

Related U.S. Application Data

[63] Continuation of Ser. No. 471,630, Mar. 3, 1983, abandoned.

[51] Int. Cl.$^4$ ............................................. A61K 31/70
[52] U.S. Cl. ................................................... 514/30
[58] Field of Search .................... 424/181, 180; 514/30

[56] References Cited

U.S. PATENT DOCUMENTS

| | | | |
|---|---|---|---|
| 3,326,759 | 6/1967 | Hamill et al. | 167/65 |
| 4,092,473 | 5/1978 | Okamoto et al. | 536/17 |
| 4,205,163 | 5/1980 | Mori et al. | 536/17 |
| 4,268,665 | 5/1981 | Sakakibara et al. | 536/17 R |
| 4,341,770 | 7/1982 | Ose et al. | 424/181 |
| 4,379,781 | 4/1983 | Hull et al. | 424/114 |

OTHER PUBLICATIONS

Derwent Abstract No. 03335B/62 of Japanese Unexamined Patent J5 3137-982, 12-1-78, (Sanraku Ocean).
Okamoto et al., "The Activity of 4"-Acylated Tylosin Derivatives Against Macrolide-Resistant Gram-Positive Bacteria", *J. Antibiotics* 32, 542-544, (1979).
Okamoto et al., "Biological Properties of New Acyl Derivatives of Tylosin", *J. Antibiotics* 33, 1309-1315, (1980).
Tsuchiya et al., "Studies of Tylosin Derivatives Effective Against Macrolide-Resistant Strains: Synthesis and Structure Activity Relationships", *J. Antibiotics* 35, 661-672, (1982).
Kirst et al., "Structure-Activity Studies Among 16-Membered Macrolide Antibiotics Related to Tylosin", *J. Antibiotics* 35 (12), 1675-1682, (1982).

*Primary Examiner*—Jerome D. Goldberg
*Attorney, Agent, or Firm*—Nancy J. Harrison; Arthur R. Whale

[57] ABSTRACT

Methods of controlling Mycoplasma infections which comprise administering to an infected or susceptible warm-blooded animal an effective amount of a new macrocin or lactenocin ester derivative of the formula:

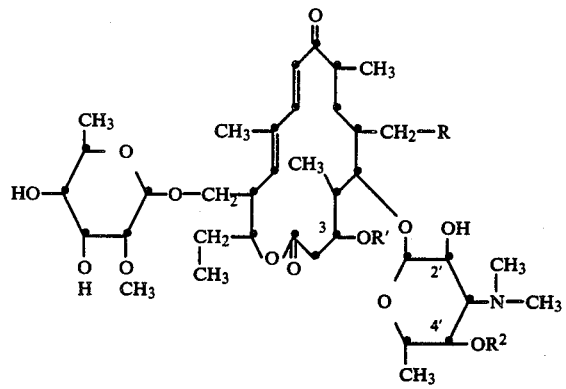

wherein R is formyl or hydroxymethyl; $R^1$ is hydrogen, acetyl or propionyl; $R^2$ is hydrogen or

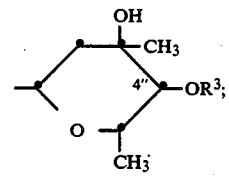

and $R^3$ is hydrogen, acetyl, propionyl, n-butyryl or isovaleryl; provided that one of $R^1$ or $R^3$ must be other than hydrogen; or a pharmaceutically acceptable acid addition salts thereof.

12 Claims, No Drawings

METHODS OF CONTROLLING MYCOPLASMA INFECTIONS

This application is a continuation of application Ser. No. 471,630, filed Mar. 3, 1983, now abandoned.

SUMMARY OF THE INVENTION

The methods of controlling Mycoplasma infections of this invention comprise administering to an infected or susceptible warm-blooded animal a compound of formula 1:

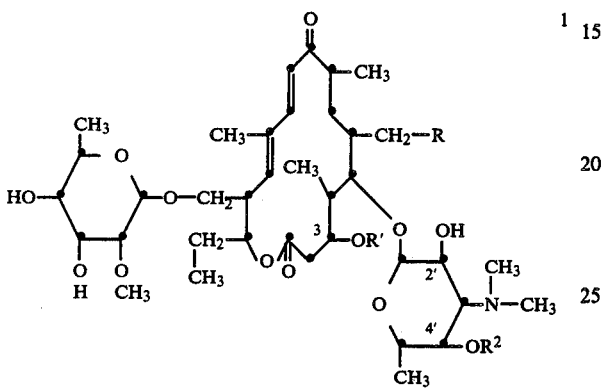

wherein R is formyl or hydroxymethyl; $R^1$ is hydrogen, acetyl or propionyl; $R^2$ is hydrogen or

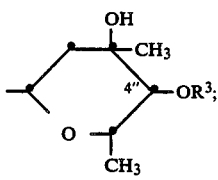

and $R^3$ is hydrogen, acetyl, propionyl, n-butyryl or isovaleryl; provided that one of $R^1$ or $R^3$ must be other than hydrogen; or a pharmaceutically acceptable acid addition salt thereof.

Mycoplasma infections cause economic losses in the veterinary field. For example, M. hyopneumonia causes chronic pneumonia in pigs (enzootic pneumonia), M. hyorhinis is a cause of polyserositis, and M. hyosynoviae is linked with arthritis in pigs. Several species of mycoplasma such as M. bovis, M. dispar and ureaplasma are associated with respiratory disease in cattle. Mycoplasmas are also suggested as agents of human diseases. Primary atypical pneumonia in children and young adults is caused by M. pneumoniae. Other diseases possibly associated with mycoplasmas include pharyngitis, wound infections, peritonitis, eye infections, salpingitis, non-gonococcal urethritis, leukemia, rheumatoid arthritis and certain autoimmune diseases. Thus, there is a need for compounds which are active against Mycoplasmas, particularly those which are active against Mycoplasma species which are resistant to known agents.

DETAILED DESCRIPTION OF THE INVENTION

We have discovered that the macrocin and lactenocin derivatives of formula 1

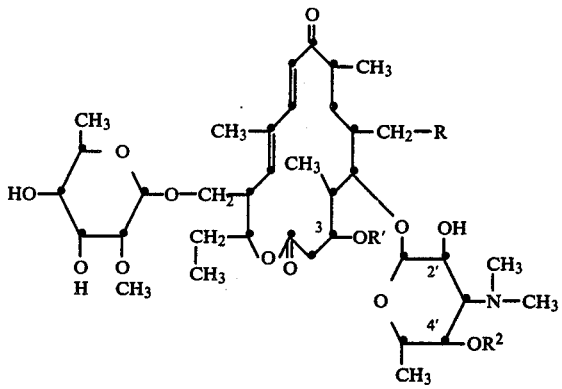

wherein R is formyl or hydroxymethyl; $R^1$ is hydrogen, acetyl or propionyl; $R^2$ is hydrogen or

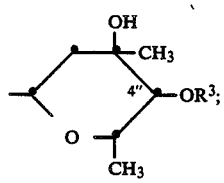

and $R^3$ is hydrogen, acetyl, propionyl, n-butyryl or isovaleryl; provided that one of $R^1$ or $R^3$ must be other than hydrogen; or a pharmaceutically acceptable acid addition salt thereof, exhibit unexpectedly good activity against Mycoplasmas. More particularly, we have discovered that these compounds are effective in vivo as well as in vitro against Mycoplasma species such as M. gallisepticum, which is the cause of major respiratory diseases in chickens and turkeys. Certain of the derivatives are active against microorganisms which are resistant to tylosin.

Thus, this invention provides methods of controlling Mycoplasma infections which comprise administering an effective amount of a compound of formula 1 to an infected or susceptible warm-blooded animal. "Controlling" as used herein means either preventing the development of the infection or treating a previously developed infection in order to minimize or eliminate the infection.

The formula 1 compounds were discovered by Jan. R. Turner, Veronica M. Krupinski, David S. Fukuda and Richard H. Baltz and are described in their copending application entitled MACROCIN DERIVATIVES AND PROCESS FOR THEIR PREPARATION, Ser. No. 471,628 filed herewith this even date.

The formula 1 compounds are prepared by contacting macrocin or lactenocin with an acyl donor in the presence of an acylating enzyme system in the form of cells or enzyme preparations. The following organisms possess the appropriate acylating enzyme system for prepararing the compounds of this invention: Streptomyces thermotolerans and strains ATCC 11416 and NRRL 15270 and Streptomyces fungicidicus subsp. espinomyceticus ATCC 21574.

The Streptomyces thermotolerans strain which is preferred for the preparation of the compounds of this invention is the subject of the copending application of Barbara B. Shreve and Jan R. Turner entitled IMPROVED BIOCONVERTING MICROORGANISM, Ser. No. 471,928, filed herewith this even data now issued U.S. Pat. No. 4,522,919. This strain has been deposited and made part of the stock culture collection of the Northern Regional Research Center, Agricultural Research, North Central Region, 1815 North University Street, Peoria, Ill., 61604, from which it is available to the public under the accession number NRRL 15270.

The compounds of formula 1 wherein R is formyl are a preferred group of compounds for the method of this invention. These compounds are prepared initially in the bioconversion reaction. The compounds of formula 1 wherein R is hydroxymethyl, which are called the "C-20-dihydro" compounds, are prepared by reduction, either chemical or biochemical, of the formula 1 compounds wherein R is formyl.

The compounds of formula 1 wherein $R^2$ is

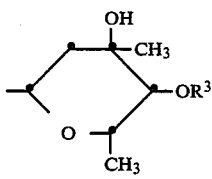

are the macrocin derivatives, which are also a preferred group for use in the methods of this invention. They are prepared when macrocin is used as the substrate in the bioconversion.

The compounds of formula 1 wherein $R^2$ is hydrogen are the lactenocin derivatives. The lactenocin derivatives can be prepared either by using lactenocin in the bioconverting reaction or by acid hydrolysis of the mycarose group from a corresponding macrocin derivative. Procedures for this type of acid hydrolysis are well known in this art.

The formula 1 compounds form acid addition salts. Those acid addition salts which are pharmaceutically acceptable are useful in this invention. Representative suitable salts include those salts formed by standard reactions with both organic and inorganic acids such as, for example, sulfuric, hydrochloric, phosphoric, acetic, succinic, citric, lactic, maleic, fumaric, palmitic, cholic, pamoic, mucic, D-glutamic, d-camphoric, glutaric, glycolic, phthalic, tartaric, formic, lauric, stearic, salicylic, methanesulfonic, benzenesulfonic, sorbic, picric, benzoic, cinnamic, and like acids.

In carrying out the methods of this invention, an effective amount of a compound of formula 1 is administered parenterally or orally to an infected or susceptible warm-blooded animal. The compounds can also be administered by insufflation, i.e. by blowing the compound, in the form of a medicated dust, into an enclosed space or room wherein the animals or poultry are held. The animals or poultry breathe the medicated dust present in the air; the medicated dust is also taken into the body through the eyes (a process called intraocular injection).

The dose which is effective to control the infection will vary with the severity of the infection and the age, weight, and condition of the animal. The total dose required for protection parenterally will generally, however, be in the range of from about 1 to about 100 mg/kg and preferably will be in the range of from about 1 to about 50 mg/kg. The dose required for oral administration will generally be in the range of from 1 to about 300 mg/kg and preferably will be in the range of from about 1 to about 100 mg/kg. Suitable dosage regimens can be constructed.

Often the most practical way to administer the compounds is by formulation into the feed supply or drinking water. A variety of feeds, including the common dry feeds, liquid feeds, and pelleted feeds, may be used.

This invention also relates to compositions useful for the control of Mycoplasma infections. These compositions comprise a compound of formula 1 together with a suitable vehicle. Compositions may be formulated for parenteral or oral administration by methods recognized in the pharmaceutical art.

The methods of formulating drugs into animal feeds are well-known. A preferred method is to make a concentrated-drug premix which in turn is used to prepare medicated feeds. Typical premixes may contain from about 1 to about 200 grams of drug per pound of premix. Premixes may be either liquid or solid preparations.

The final formulations of feeds for animals or poultry will depend upon the amount of drug to be administered. The common methods of formulating, mixing, and pelleting feeds may be used to prepare feeds containing a compound of formula 1.

Effective injectable compositions containing these compounds may be in either suspension or solution form. In the preparation of suitable formulations it will be recognized that, in general, the water solubility of the acid addition salts is greater than that of the free bases. Similarly, the bases are more soluble in dilute acids or in acidic solutions than in neutral or basic solutions.

In the solution form the compound is dissolved in a physiologically acceptable vehicle. Such vehicles comprise a suitable solvent, preservatives such as benzyl alcohol, if needed, and buffers. Useful solvents include, for example, water and aqueous alcohols, glycols, and carbonate esters such as diethyl carbonate. Such aqueous solutions contain, in general, no more than 50% of the organic solvent by volume.

Injectable suspension compositions require a liquid suspending medium, with or without adjuvants, as a vehicle. The suspending medium can be, for example, aqueous polyvinylpyrrolidone, inert oils such as vegetable oils or highly refined mineral oils, or aqueous carboxymethylcellulose.

Suitable physiologically acceptable adjuvants are necessary to keep the compound suspended in suspension compositions. The adjuvants may be chosen from among thickeners such as carboxymethylcellulose, polyvinylpyrrolidone, gelatin, and the alginates. Many surfactants are also useful as suspending agents. Lecithin, alkylphenol polyethylene oxide adducts, naphthalenesulfonates, alkylbenzenesulfonates, and the polyoxyethylene sorbitan esters are useful suspending agents.

Many substances which affect the hydrophilicity, density, and surface tension of the liquid suspending medium can assist in making injectable suspensions in individual cases. For example, silicone antifoams, sorbitol, and sugars can be useful suspending agents.

The compounds used in this invention exhibit unexpectedly good antibiotic activity against Mycoplasma species, both in vitro and in vivo. For example, Table 1 summarizes the minimal inhibitory concentrations (MIC's) at which illustrative compounds inhibit certain Mycoplasma strains. The MIC's in Table I were obtained using a conventional broth-dilution microtiter test.

TABLE I

Activity of Formula 1 Compounds vs. Mycoplasma

| Test Organism | MIC (mcg/ml) Values of Test Compounds | | | |
|---|---|---|---|---|
| | 3-Acetyl-macrocin | 3-Acetyl-4''-(n-Butyryl)-macrocin | 3-Acetyl-4''-Isovaleryl-macrocin | 3-Acetyl-lactenocin |
| *Mycoplasma gallisepticum* 38502[a] | 0.78 | 0.195 | ≦0.048 | 0.78 |
| *Mycoplasma gallisepticum* 34159[b] | 50 | 6.25 | 3.12 | >50 |
| *Mycoplasma gallisepticum* 41313[b] | 50 | 3.12 | 3.12 | 50 |
| *Mycoplasma synoviae* 46995 | 0.39 | ≦0.048 | ≦0.048 | 0.39 |
| *Mycoplasma hyorhinis* S-41313 | 6.25 | 0.39 | 0.39 | 25 |
| *Mycoplasma hyopneumoniae* S-5972 | NT[c] | 0.048 | 0.048 | NT |

[a]Tylosin-susceptible strain.
[b]Tylosin-resistant strain.
[c]NT = Not tested

In order to illustrate more fully the operation of this invention, the following examples are provided:

PREPARATION 1

Bioconversion of Macrocin to 3-O-Acetylmacrocin, Acetyl-4''-O-(n-Butyryl)macrocin and 3-O-Acetyl-4''-O-Isovalerylmacrocin by a Mutant of *Streptomyces thermotolerans*

A. Inoculum Preparation

Suitable vegetative inoculum may be obtained by inoculating sterilized medium with lyophilized spore suspensions or spore suspensions obtained by scraping spores from a well sporulated slant of *Streptomyces thermotolerans* NRRL 15270; best results, however, have been obtained using cultures inoculated from a standardized vegetative inoculum that has been preserved in liquid nitrogen. Liquid-nitrogen-stock inoculum is prepared in the following manner:

A lyophile pellet of *S. thermotolerans* NRRL 15270 is suspended in sterile water (2 ml). The resulting spore suspension is inoculated into 50 ml of sterile medium in a 250-ml wide-mouth Erlenmeyer flask at a rate of 0.4 % volume/volume (v/v). The medium has the following composition:

| Vegetative Medium Composition (CSI) | |
|---|---|
| Ingredient | Amount |
| Glucose | 25 g |
| Soybean grits | 15 g |
| Blackstrap molasses | 3 g |
| Enzyme-hydrolyzed casein[a] | 1 g |
| CaCO$_3$ | 2.5 g |
| Czapek's Mineral Stock[b] | 2 ml |
| Deionized H$_2$O to a total of | one liter |
| pH adjusted to 7.2 prior to sterilization; autoclave 45 minutes | |

[a]Amber EHC (Amber Laboratories, Juneau, WI)
[b]Czapek's Mineral Stock

| | |
|---|---|
| KCl | 100 g |
| MgSO$_4$.7H$_2$O | 100 g |
| Deionized Water | 900 ml |

FeSO$_4$.7H$_2$O (2 g) was dissolved in 100 ml distilled water containing 2 ml of concentrated HCl. This solution was added to the above KCl/MgSO$_4$.7H$_2$O solution to complete preparation of the Czapek's Minerals.

Flasks containing inoculated media are maintained at 37° C. on a rotary shaker agitating in a 2-inch-diameter arc at 260 RPM for 24 hours. The vegetative culture is then harvested, diluted 1:1 (volume:volume) with a sterile suspending agent of glycerol:lactose:water (2:1:7) and dispensed into sterile tubes (2 ml/tube). The diluted inoculum is then stored over liquid nitrogen in appropriate storage containers and used as a working-stock inoculum for the cultivation of shake-flask conversion cultures and fermenter seed inoculum.

B. General Shake-flask Conversion Procedure

Shake-flask conversions are generally conducted with a culture-volume to flask-volume ratio of 1/5. Sterilized CSI medium is inoculated with liquid-nitrogen-preserved stock inoculum at a rate of 0.4% v/v and incubated at 37° C. on a rotary shaker with a 2-inch-diameter arc at 260 RPM for 22–24 hours. A concentrated methanolic solution containing macrocin and a sterilized, neutralized solution containing DL-norvaline and L-leucine are then added to the converting culture at respective final concentrations of 0.5 mg macrocin/ml and 1.0 mg of each amino acid/ml. The culture is incubated an additional 24 hours as described supra and then is harvested. Conversion-products are recovered by adjusting the pH of the whole culture to about pH 8.5–9.0 and repeatedly extracting with equal volumes of ethyl acetate. Extracts are combined and concentrated under vacuum to dryness. The various conversion products are recovered in purified form via reversed-phase (RP) high performance liquid chromatography (HPLC).

In general, shake-flask conversions result in complete conversion of substrate to the corresponding 3-O-acetyl derivative in 8–10 hours, followed by subsequent conversion of the 3-O-acetyl intermediate to the 3-O-acetyl-4''-O-(n-butyryl) and/or 3-O-acetyl-4''-O-isovaleryl derivatives. Extension of the conversion time beyond 24–28-hours results in the partial conversion of products to the C-20 dihydro-derivative.

C. General Procedure for Conversion in Stirred Fermenters

Seed inoculum for stirred fermenters (tanks) is prepared by inoculating 200 ml of sterile CSI medium in a one-liter wide-mouth Erlenmyer flask with liquid-nitrogen-stock inoculum at a rate of 0.4% v/v. The seed culture is then incubated at 37° C. on a rotary shaker with a 2-inch diameter arc at 260 RPM for 22 hours. The resulting vegetative culture is used to inoculate a stirred fermenter containing 25 liters of sterile medium (0.8% inoculum, v/v) which has the following composition:

| Tank Fermentation Medium | |
|---|---|
| Ingredient | Amount |
| Antifoam agent[a] | 0.2 g |
| Glucose | 25 g |
| Soybean grits | 15 g |
| Blackstrap molasses | 3 g |
| Casein | 1 g |

-continued

| Tank Fermentation Medium | |
|---|---|
| Ingredient | Amount |
| CaCO$_3$ | 5 g |
| Czapek's Mineral Stock | 2 ml |
| Deionized water q.s. to | 1 liter |

[a]Dow Corning (Chicago, IL)
Sterilize for 45 minutes at about 126° C. and 20-23 psi Fermentation temperature is maintained at 37° C. Two 6-blade 6-inch-diameter impellers mounted on the fermenter impeller shaft are rotated at 300 RPM to provide agitation. The culture is aerated by sparging sterile air into the fermenter below the bottom impeller at a rate of 0.5 v/v/m. Sterilized, neutralized solutions (2 L.) containing DL-norvaline (25 g), L-leucine (25 g) and 50-100 ml of a solution of macrocin (12.5 g) in methanol are added to the culture after 22-24 hours of growth. Fermentation is continued for an additional 22-24 hours, although in most cases conversion is complete in 12-16 hours.

Macrocin is rapidly converted to 3-O-acetyl macrocin, usually within three hours after substrate addition. Conversion of 3-O-acetyl macrocin to the 3-O-acetyl-4″-O-(n-butyryl)macrocin and 3-O-acetyl-4″-O-isovalerylmacrocin derivatives occurs at a somewhat slower rate. Maximum 4″-ester formation usually occurs about 7-16 hours after substrate addition. When the converting culture is harvested about 7-8 hours after substrate addition, conversion to the 3,4″-diester is approximately 85-95% complete and formation of the C-20-dihydro products is minimized.

When preparing 3-O-acetyl-4″-O-isovalerylmacrocin, it is preferable to add L-leucine (50 g per 25 liters of culture) to the medium.

When C-20-dihydro compounds are desired, the fermentation is carried out for a longer period of time, preferably from about 22 to about 30 hours.

D. Assay Procedure

This assay method is useful for monitoring the bioconversion process and for isolating the individual bioconversion products: A sample (4 ml) of whole broth containing bioconversion product(s) is adjusted to pH 9.0 with NaOH and extracted once with ethyl acetate (2 ml). The resulting suspension is centrifuged, and the ethyl acetate portion is analyzed by reversed-phase HPLC, using Waters μ-Bondapak C-18 or Merck Li-Chrosorb RP-18 as the adsorbent. 3-O-Acetylmacrocin is assayed using the solvent system H$_2$O/MeOH/NH$_4$COOH (40/60/0.2), while the 3,4′-diesters are assayed with the system H$_2$O/MeOH/NH$_4$COOH (25/75/0.2). Macrocin and the ester derivatives are detected by ultraviolet (UV) absorption at 280 nm.

E. Isolation of Conversion Products

The pH of the fermentation broth is adjusted to about 8.5 with sodium hydroxide. Ethyl acetate (two volumes) is added with vigorous stirring. The resulting emulsion is passed through a Sepa centrifuge to sediment cellular debris and break the emulsion. Cell debris and the aqueous phase are discarded. The organic layer is concentrated under vacuum to an oily residue which is repeatedly triturated with hexane until an oil-free dry crude preparation is obtained. The yield of crude preparation is in the range of 3-9 g.

The crude dried preparation is subjected to repeated purification via reverse-phase HPLC until the appropriate derivative is obtained in pure form.

Initially, 3-O-acetylmacrocin is separated from the diesters by preparative HPLC (Waters Prep/500-reversed-phase) of crude dried extract (in amounts of about 3-7 g), using the solvent system H$_2$O/CH$_3$CH/diethylamine (65/35/0.1). Diesters are partially separated from each other using the system H$_2$O/CH$_3$CN/pyridine/HOAc (65/35/1.5/0.5). Appropriate fractions, as determined by UV at 280 nm and analytical HPLC, are combined, concentrated to the aqueous phase and lyophilized to yield dry preparations.

The mono- and diesters are further purified by HPLC with either 38″×½″ or 25.5″×1″ LP-1/C$_{18}$ columns with the appropriate solvent system:

| Compound | Solvent System | Ratio |
|---|---|---|
| 3-O—acetylmacrocin | H$_2$O/CH$_3$CN/NH$_4$HCO$_3$ | (70/30/0.001) |
| 3-O—acetyl-4″-O—(n-butyryl)macrocin and 3-O—acetyl-4″-O—isovalerylmacrocin | H$_2$O/CH$_3$CN/pyridine/HOAc | (70/30/1.5/0.5) |

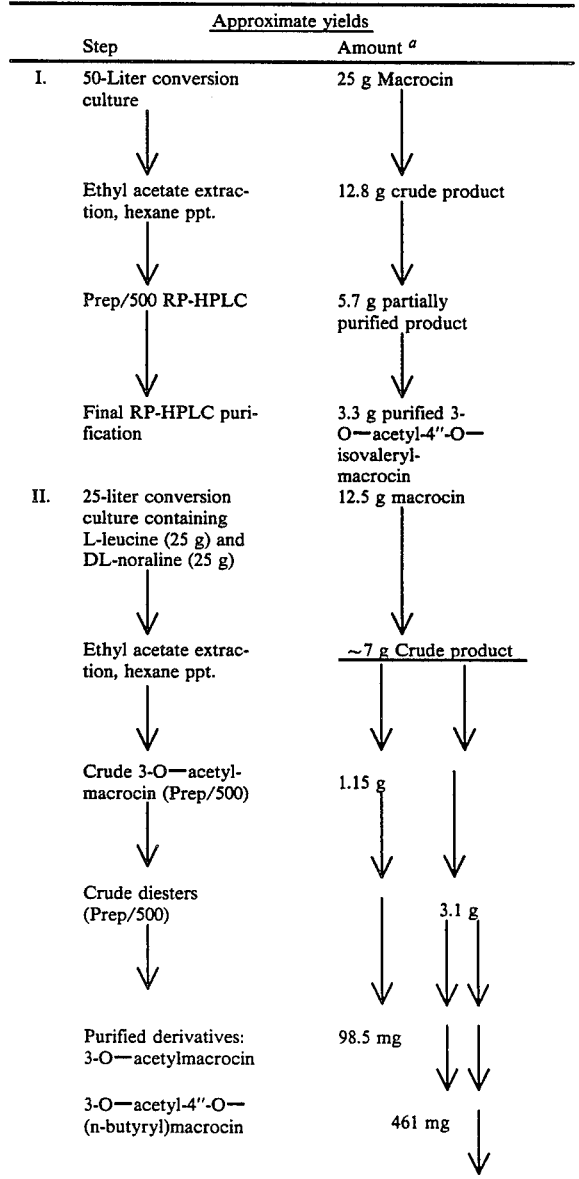

| -continued | |
|---|---|
| 3-O—acetyl-4"-O—iso-valerylmacrocin | 548 mg |

PREPARATION 2

Preparation of 3-O-Acetyllactenocin

3-O-Acetylmacrocin (350 mg) was added to 1N sulfuric acid (43 ml). The resulting solution was stirred for about one hour at room temperature and then neutralized with concentrated aqueous NaHCO$_3$ solution (to about pH 7.5). The pH of this solution was adjusted to 8.5 by the addition of NaOH; the solution was then extracted five times with ethyl acetate (equal volumes). The ethyl acetate extracts were combined, dried over anhydrous Na$_2$SO$_4$, and evaporated to yield crude 3-O-acetyllactenocin (302.5 mg). This material was purified by HPLC using a 38-inch×½-inch LP-1/C$_{18}$ silica-gel column and eluting with a H$_2$O/CH$_3$CN/pyridine/HOAc (78.4/19.6/1.5/0.5) solvent system at a flow rate of about 5 ml/minute. Appropriate fractions, identified by analytical HPLC using a solvent system of H$_2$O/CH$_3$CN (3:1) containing 2% pyridinium acetate, were combined and evaporated to give 165.5 mg of 3-O-acetyllactenocin.

EXAMPLE 1

Use of Formula 1 Compounds vs. *Mycoplasma gallisepticum* Infection in Chickens The compounds of this invention have exhibited in vivo activity against experimental infections caused by *Mycoplasma gallisepticum*. In these tests infections were induced in chicks by injecting 0.2 ml of a broth culture of *M. gallisepticum* into the abdominal air sac of one- to three-day-old chicks. The compounds were administered by gavage at a dose equivalent to 0.5 g/gal two times on the day of infection, two times on the day following infection and one time on the third day. Twenty-one days after infection the chicks were weighed, a blood sample was taken, and the chicks were sacrificed. The presence or absence of air-sac lesions was recorded. The results of these tests are summarized in Table II.

TABLE II

Antimycoplasmal Activity of Macrocin Derivatives in Chicks

| Test Compound | Dosage Level | Mortality | *Mycoplasma gallisepticum* Number with Air-Sac Lesions/Number Treated | Number with Antibodies[a]/Number Tested |
|---|---|---|---|---|
| 3-Acetyl-4"-(n-butyryl)-macrocin | 0.5 g/gal × 5 | 1/7 | 7/10 | 7/9 |
| 3-Acetyl-4"-isovaleryl-macrocin | 0.5 g/gal × 5 | 0/10 | 1/10 | 10/10 |
| Infected Control | 0 | 2/7 | 10/10 | 10/10 |
| Uninfected Control | 0 | 0/10 | 0/10 | 0/10 |

[a]Antibodies to *M. gallisepticum*

EXAMPLE 2

Injectable Formulations (A) A formula 1 base is added to propylene glycol. Water and benzyl alcohol are added so that the solution contains 50% (by volume) propylene glycol, 4% (by volume) benzyl alcohol, and 200 mg/ml of a formula 1 base.

(B) A solution is prepared as described in Section A except that the solution contains 50 mg/ml of a formula 1 base.

(C) A solution is prepared as described in Section A except that the solution contains 350 mg/ml of a formula 1 base.

(D) A solution is prepared as described in Section A except that the solution contains 500 mg/ml of a formula 1 tartrate.

(E) A suspension is prepared by adding a finely ground formula 1 compound to carboxymethyl cellulose with thorough mixing so that the suspension contains 200 mg of the formula 1 base per ml of suspension.

EXAMPLE 3

Chick Ration for Control of Mycoplasma

A balanced, high-energy ration adapted to feed chicks for rapid weight gain is prepared by the following recipe:

| Ingredient | Percent | Lbs/Ton |
|---|---|---|
| Ground yellow corn | 53.46 | 1069.2 |
| Soybean meal, solvent-extracted dehulled, finely ground, 48 percent protein | 31.73 | 634.6 |
| Animal-vegetable fat | 2.83 | 56.6 |
| Dried fish meal | 5.0 | 100 |
| Distillers' solubles from corn | 4.0 | 80 |
| Dicalcium phosphate, feed grade | 1.28 | 25.6 |
| Ground limestone | 0.62 | 12.4 |
| Salt | 0.3 | 6.0 |
| Vitamin premix[1] | 0.5 | 10 |
| Trace mineral premix[2] | 0.1 | 2 |
| 2-Amino-4-hydroxybutyric acid (hydroxy analog of methionine) | 0.17 | 3.4 |
| Formula 1 compound | 0.01 | 0.2 |

[1]Vitamin premix provides 3000 IU of vitamin A, 900 ICU of vitamin D$_3$, 40 mg of vitamin E, 0.7 mg of vitamin K, 1000 mg of choline, 70 mg of niacin, 4 mg of pantothenic acid, 4 mg of riboflavin, 100 mcg of vitamin B$_{12}$, 100 mcg of biotin and 125 mg of ethoxyquin per kg of complete feed.
[2]Trace mineral premix provides 75 mg of manganese, 50 mg of zinc, 25 mg of iron and 1 mg of iodine per kg of complete feed.

These substances are mixed in accordance with standard feed-mixing techniques. Chicks fed such a ration, with water ad libitum, are protected against exposure to mycoplasmal infections.

We claim:

1. a method for controlling Mycoplasma infections which comprises administering to a warm-blooded animal a composition comprising an amount effective to control Mycoplasma infections of a compound of the formula

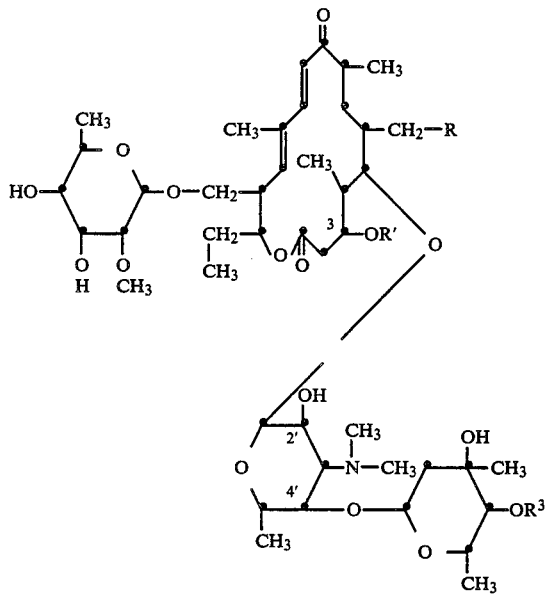

wherein
R is formyl or hydroxymethyl;
R[1] is hydrogen, acetyl or propionyl; and R[3] is hydrogen, acetyl, propionyl, n-butyryl or isovaleryl; provided that one of R[1] or R[3] must be other than hydrogen; or a pharmaceutically acceptable acid addition salt thereof; together with a suitable pharmaceutical vehicle.

2. The method of claim 1 wherein the compound is one wherein R is formyl.

3. The method of claim 1 wherein the compound is one wherein R[1] is acetyl.

4. The method of claim 1 wherein the compound is one wherein R[3] is hydrogen.

5. The method of claim 1 wherein the compound is one wherein R[3] is n-butyryl.

6. The method of claim 1 wherein the compound is one wherein R[3] is isovaleryl.

7. The method of claim 1 wherein the vehicle is aqueous propylene glycol.

8. The method of claim 1 wherein the composition is administered as a single injection.

9. The method of claim 1 wherein divided doses of the composition are administered in a series of injections.

10. The method of claim 1 wherein the composition is administered orally.

11. A method for controlling Mycoplasma infections which comprises administering to a warm-blooded animal a composition comprising an amount effective to control Mycoplasma infections of a compound of the formula

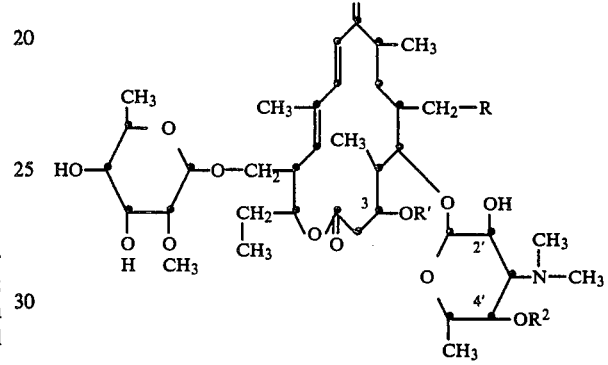

wherein
R is formyl or hydroxymethyl; and
R[1] is acetyl or propionyl;
or a pharmaceutically acceptable acid addition salt thereof; together with a suitable pharmaceutical vehicle.

12. The method of claim 1 wherein the composition is administered orally.

* * * * *

UNITED STATES PATENT AND TRADEMARK OFFICE
CERTIFICATE OF CORRECTION

PATENT NO. : 4,594,337
DATED : June 10, 1986
INVENTOR(S) : Earl E. Ose and Jan R. Turner It is certified that error appears in the above—identified patent and that said Letters Patent is hereby corrected as shown below:

Column 10, line 43, "1. a method" should read -- 1. A method --.

Column 11, lines 8-18, that portion of the structural formula appearing as

" 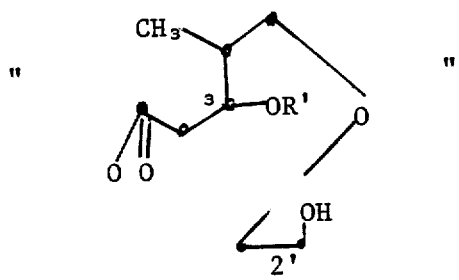 "

should read

-- 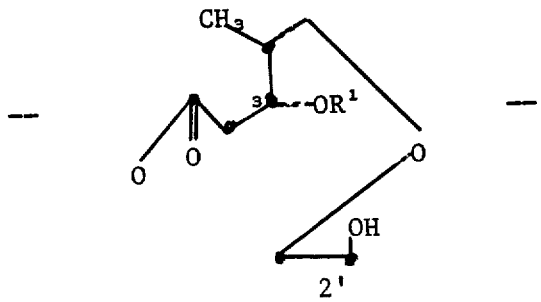 --

UNITED STATES PATENT AND TRADEMARK OFFICE
CERTIFICATE OF CORRECTION

PATENT NO. : 4,594,337
DATED : June 10, 1986
INVENTOR(S) : Earl E. Ose and Jan R. Turner It is certified that error appears in the above—identified patent and that said Letters Patent is hereby corrected as shown below:

Column 12, lines 23-28, that portion of the structural formula appearing as

"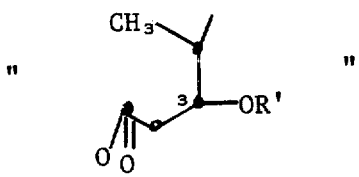"

should read

-- 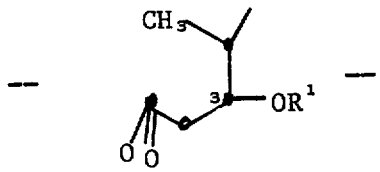 --

Column 12, lines 28-32, that portion of the structural formula appearing as

"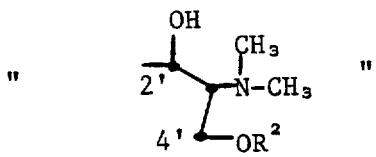"

UNITED STATES PATENT AND TRADEMARK OFFICE
CERTIFICATE OF CORRECTION

PATENT NO. : 4,594,337

DATED : June 10, 1986

INVENTOR(S) : Earl E. Ose and Jan R. Turner

It is certified that error appears in the above-identified patent and that said Letters Patent is hereby corrected as shown below:

should read — 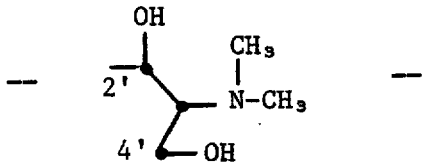 —

Signed and Sealed this

Second Day of February, 1988

*Attest:*

DONALD J. QUIGG

*Attesting Officer*  *Commissioner of Patents and Trademarks*